US008206923B2

(12) United States Patent
Garza Gonzalez et al.

(10) Patent No.: US 8,206,923 B2
(45) Date of Patent: Jun. 26, 2012

(54) METHOD FOR DETECTION AND MULTIPLE, SIMULTANEOUS QUANTIFICATION OF PATHOGENS BY MEANS OF REAL-TIME POLYMERASE CHAIN REACTION

(76) Inventors: Elvira Garza Gonzalez, Guadalupe (MX); Francisco Javier Bosques Padilla, Monterrey (MX); Victor Manuel Moreno Campana, Monterrey (MX)

( * ) Notice: Subject to any disclaimer, the term of this patent is extended or adjusted under 35 U.S.C. 154(b) by 203 days.

(21) Appl. No.: 12/298,298

(22) PCT Filed: Apr. 19, 2007

(86) PCT No.: PCT/MX2007/000052
§ 371 (c)(1),
(2), (4) Date: Oct. 23, 2008

(87) PCT Pub. No.: WO2007/123386
PCT Pub. Date: Nov. 1, 2007

(65) Prior Publication Data
US 2010/0159448 A1 Jun. 24, 2010

(30) Foreign Application Priority Data
Apr. 24, 2006 (MX) .................... NL/A/2006/000028

(51) Int. Cl.
*C12Q 1/68* (2006.01)
*C12P 19/34* (2006.01)
*C07H 21/04* (2006.01)
(52) U.S. Cl. ................... 435/6.12; 435/91.2; 536/24.32; 536/24.33
(58) Field of Classification Search ............. 435/6, 91.2; 536/24.32, 24.33
See application file for complete search history.

(56) References Cited

U.S. PATENT DOCUMENTS

| | | | |
|---|---|---|---|
| 5,401,631 A | 3/1995 | Lane et al. | |
| 5,654,417 A * | 8/1997 | Tarr et al. | 536/24.32 |
| 6,372,424 B1 * | 4/2002 | Brow et al. | 435/5 |
| 6,677,152 B2 | 1/2004 | Fisher | |
| 2003/0054436 A1 * | 3/2003 | Kunsch et al. | 435/69.1 |
| 2004/0018514 A1 * | 1/2004 | Kunst et al. | 435/6 |
| 2004/0248148 A1 | 12/2004 | Horgen | |
| 2005/0227275 A1 * | 10/2005 | Jung et al. | 435/6 |
| 2006/0051769 A1 | 3/2006 | Barts | |

FOREIGN PATENT DOCUMENTS

WO WO2005014857 A 2/2005
WO WO 2006032500 A2 * 3/2006

OTHER PUBLICATIONS

Database EMBL [Online] Sep. 21, 2002, "Universal eubacteria nucleic acid probe and method." XP002556871 retrieved from EBI accession No. EMBL:BD140320 Database accession No. BD140320.
Database EMBL [Online] Feb. 21, 2004, "Seqence 28 from patent US 6677153." XP002556872 retrieved from EBI accession No. EMBL:AR452382.
Database Geneseq [Online] Mar. 9, 2006, "*Escherichia coli* nucleic acid probe SEQ ID No. 190038." XP002556873 retrieved from EBI accession No. GSN:AFE63324 Database accession No. AFE63324.
Kamel A. Abd-Elsalam; Bioinformatic tools and guideline for PCR primer design; African Journal of Biotechnology vol. 2 (5), pp. 91-95, May 2003; Molecular Markers Lab., Plant Pathology Research Institute, Agricultural Research Center, Orman 12619, Giza, Egypt.
S. A. Ballard, E. A. Grabsch, P. D. R. Johnson, M. L. Grayson; Comparison of Three PCR Primer Sets for Identification of vanB Gene Carriage in Feces and Correlation with Carriage of Vancomycin-Resistant *Enterococci*: Interference by vanB-Containing Anaerobic Bacilli; Antimicrobial Agents and Chemotherapy, Jan. 2005, p. 77-81; American Society for Microbiology; Infectious Diseases and Microbiology Depts., Austin Health, Dept. of Medicine, Univ. of Melbourne, and Dept. of Epidemiology and Preventive Medicine, Monash University, Melbourne, Australia.
A. T. Csordas, J. D. Barak, M. J. Delwiche; Comparison of primers for the detection of *Salmonella enterica* serovars using real-time PCR; Letters in Applied Microbiology 2004, 39, 187-193; The Society of Applied Microbiology; Department of Biological and Agricultural Engineering, University of California at Davis, Davis, CA, and Produce Safety and Microbiology Research Unit, USDA Agricultural Research Service, Albany, CA, USA.
Elfath M. Elnifro, Ahmed M. Ashshi, Robert J. Cooper, Paul E. Klapper; Multiplex PCR: Optimization and Application in Diagnostic Virology; Clinical Microbiology Reviews, Oct. 2000, p. 559-570; American Society for Microbiology; School of Medicine, The University of Manchester, and Clinical Virology, Central Manchester Healthcare Trust, Manchester, United Kingdom.
Ladeana Hillier, Philip Green; OSP: A Computer Program for Choosing PCR and DNA Sequencing Primers; Genome Research 1991, p. 1:124-128; Cold Springs Harbor Laboratory Press; Genetics Department, Washington University School of Medicine St. Louis, Missouri 63110.
Tichopad A., Didier A., Pfaff; M. W.; Inhibition of real-time RT-PCR quantification due to tissue-specific contaminants; Mol. Cell Probes, Feb. 2004, p. 18(1):45-50; Institute of Physiology, FML-Weihenstephan, Center of Life and Food Science, Technical University of Munich, Germany.

* cited by examiner

*Primary Examiner* — Prabha Chunduru
(74) *Attorney, Agent, or Firm* — Parsons & Goltry; Michael W. Goltry; Robert A. Parsons (57) ABSTRACT

A method for multiple and simultaneously detecting and quantifying of *Listeria* spp, *Staphylococcus aureus*, *Campylobacter jejuni*, and *Escherichia coli* 0157:H7, by extracting DNA from a sample; preparing a reaction mixture for enzymatic amplification of the extracted DNA and sets of pairs of oligonucleotide primers identified as SEQ ID No. 1 and SEQ ID No. 2, SEQ ID No. 4 and SEQ ID No. 5, SEQ ID No. 7 and SEQ ID No. 8, and SEQ ID No. 10 and SEQ ID No. 11, and probes with oligonucleotide sequences identified as SEQ ID No. 3, SEQ ID No. 6, SEQ ID No. 9 and SEQ ID No. 12; providing a thermostable DNA polymerase and magnesium salt to the reaction mixture; amplifying the reaction mixture by a PCR reaction; and determining the presence or absence, and quantification of the pathogens by using a fluorescent signal or fluorescence emission specific for each pathogen.

5 Claims, 4 Drawing Sheets

SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: Oligonucleotide "upstream" F of Listeria sp

<400> SEQUENCE: 1
cttgacatcc tttgaccact ctg                                               23

<210> SEQ ID NO 2
<211> LENGTH: 23
<212> TYPE: DNA
<213> ORGANISM: Artificial
<220> FEATURE:
<223> OTHER INFORMATION: Oligonucleotide "downstream" R of Listeria sp

<400> SEQUENCE: 2
gacttaaccc aacatctcac gac                                               23

<210> SEQ ID NO 3
<211> LENGTH: 24
<212> TYPE: DNA
<213> ORGANISM: Artificial
<220> FEATURE:
<223> OTHER INFORMATION: Oligonucleotide of probe P of Listeria sp

<400> SEQUENCE: 3
agctgacgac aaccatgcac cacc                                              24

<210> SEQ ID NO 4
<211> LENGTH: 24
<212> TYPE: DNA
<213> ORGANISM: Artificial
<220> FEATURE:
<223> OTHER INFORMATION: Oligonucleotide "upstream" F of Staphylococcus
      aureus

<400> SEQUENCE: 4
aacaaaacag accatcttta agcg                                              24

<210> SEQ ID NO 5
<211> LENGTH: 24
<212> TYPE: DNA
<213> ORGANISM: Artificial
<220> FEATURE:
<223> OTHER INFORMATION: Oligonucleotide "downstream" R of
      Staphylococcus aureus

<400> SEQUENCE: 5
agatgagcta ccttcaagac cttc                                              24

<210> SEQ ID NO 6
<211> LENGTH: 24

-continued

```
<212> TYPE: DNA
<213> ORGANISM: Artificial
<220> FEATURE:
<223> OTHER INFORMATION: Oligonucleotide of probe P of Staphylococcus
      aureus

<400> SEQUENCE: 6
actcaaccga cgacaccgaa ccct                                            24

<210> SEQ ID NO 7
<211> LENGTH: 21
<212> TYPE: DNA
<213> ORGANISM: Artificial
<220> FEATURE:
<223> OTHER INFORMATION: Oligonucleotide "upstream" F of Campylobacter
      jejuni

<400> SEQUENCE: 7
gcagcagtag ggaatattgc g                                               21

<210> SEQ ID NO 8
<211> LENGTH: 22
<212> TYPE: DNA
<213> ORGANISM: Artificial
<220> FEATURE:
<223> OTHER INFORMATION: Oligonucleotide "downstream" R of Campylobacter
      jejuni

<400> SEQUENCE: 8
tacgctccga aaagtgtcat cc                                              22

<210> SEQ ID NO 9
<211> LENGTH: 22
<212> TYPE: DNA
<213> ORGANISM: Artificial
<220> FEATURE:
<223> OTHER INFORMATION: Oligonucleotide of probe P of Campylobacter
      jejuni

<400> SEQUENCE: 9
aaccctgacg cagcaacgcc gc                                              22

<210> SEQ ID NO 10
<211> LENGTH: 24
<212> TYPE: DNA
<213> ORGANISM: Artificial
<220> FEATURE:
<223> OTHER INFORMATION: Oligonucleotide "upstream" F of Escherichia
      coli

<400> SEQUENCE: 10
gcagataaac tcatcgaaac aagg                                            24

<210> SEQ ID NO 11
<211> LENGTH: 24
<212> TYPE: DNA
<213> ORGANISM: Artificial
<220> FEATURE:
<223> OTHER INFORMATION: Oligonucleotide "downstream" R of Escherichia
      coli

<400> SEQUENCE: 11
taaattaatt ccacgccaac caag                                            24

<210> SEQ ID NO 12
<211> LENGTH: 24
<212> TYPE: DNA
<213> ORGANISM: Artificial
```

-continued

<220> FEATURE:
<223> OTHER INFORMATION: Oligonucleotide of probe P of Escherichia coli

<400> SEQUENCE: 12
accctgtcca cacgatgcca atgt                                            24

METHOD FOR DETECTION AND MULTIPLE, SIMULTANEOUS QUANTIFICATION OF PATHOGENS BY MEANS OF REAL-TIME POLYMERASE CHAIN REACTION

TECHNICAL FIELD OF THE INVENTION

The present invention is related, in general, to the detection, identification, and quantification of pathogenic bacteria, and particularly to a method for the detection and multiple, simultaneous quantification of any combination of pathogens, such as *Listeria* spp, *Staphylococcus aureusm Campylobacter jejuni* and/or *Escherichia coli* O157:H7, by means of multiplex amplification reaction, using real-time polymerase chain reaction.

BACKGROUND OF THE INVENTION

At present, the detection of pathogenic bacteria transmissible by food, such as *Listeria* spp, *Staphylococcus aureus, Campylobacter jejuni* and *Escherichia coli* O157:H7, is a very important task in the field of medicine and public health and is very important in the agro-foodstuffs, both for the producer and the distributor of food products (raw materials and/or processed products), for which several methods have been described for their detection and identification.

One of the current methodologies, considered among the most effective in the detection, identification and quantification of pathogens, is the one that is based on molecular techniques, as the method of polymerase chain reaction, commonly known as PCR. The PCR procedure is generally regarded as the most sensitive and rapid method used to detect nucleic acids of pathogens in a given sample test in particular, and we can find it described within the state of the art by Kary B. Mullis et al. in the family of U.S. Pat. No. 4,683,195, U.S. Pat. No. 4,683,202, U.S. Pat. No. 4,800,159, U.S. Pat. No. 4,889,818, U.S. Pat. No. 4,965,188, U.S. Pat. No. 5,008,182, U.S. Pat. No. 5,038,852, U.S. Pat. No. 5,079,352, U.S. Pat. No. 5,176,995, U.S. Pat. No. 5,310,652, U.S. Pat. No. 5,310,893, U.S. Pat. No. 5,322,770, U.S. Pat. No. 5,333,675, U.S. Pat. No. 5,352,600, U.S. Pat. No. 5,374,553, U.S. Pat. No. 5,386,022, U.S. Pat. No. 5,405,774, U.S. Pat. No. 5,407,800, U.S. Pat. No. 5,418,149, U.S. Pat. No. 5,420,029 among others.

To perform the PCR technique, basically, you need at least one pair of oligonucleotides for each of the pathogens to be identified, so that each pair of primers include a first nucleotide sequence complementary to a sequence that borders on the extreme 5' of a sequence of a nucleic acid target and a second nucleotide sequence complementary to a sequence that borders the 3' end of the sequence of nucleic acid target. Nucleotide sequences should have every pair of oligonucleotide primers which are specific to the pathogen to be detected, so that they do not react or are crossed with other pathogens.

As the PCR technique is a sensitive and quick method to detect pathogens on an individual basis, this can also be used to simultaneously detect multiple pathogens present in a sample. However, the PCR methodology used for simultaneous detection of multiple pathogens in a sample is problematic, since its main obstacle lies in the cross reaction that may be present due to the use of multiple nucleotide sequences in order to have the preferential amplification of certain target sequences, present in the sample at the expense of other target sequences, also present.

Examples of multiple and simultaneous detection of pathogens, using the PCR methodology, are described by John W. Czajka in the issuance of international patent application WO-0314704, and by Linxian Wo and others in the family of U.S. Pat. No. 5,612,473, U.S. Pat. No. 5,738,995, U.S. Pat. No. 5,753,444, U.S. Pat. No. 5,756,701, and U.S. Pat. No. 5,846,783.

The publication of international patent application WO-0314704 describes a method to detect specific and simultaneously pathogen species of *Campylobacter* in a complex test sample. The pathogen species of *Campylobacter* to be detected may be *Campylobacter jejuni* or *Campylobacter coli*. The complex test sample can be a sample of food, water or a rich array of food. The method uses the PCR amplification with or without an internal positive control and appropriate pairs of primers. Multiple species can be detected in said reaction.

In the family of U.S. Pat. No. 5,612,473, U.S. Pat. No. 5,738,995, U.S. Pat. Nos. 5,753,444, 5,756,701, and U.S. Pat. No. 5,846,783 a multiplex PCR method is described to detect infectious agents quickly and simultaneously in one sample. The infectious agents that are detected, are *Salmonella* spp, *Shigella* spp, *Campylobacter* spp, *Yersinia* spp and *Escherichia coli*, in particular *Escherichia coli* O157:H7. The limitation of the method described in these patents is that it allows a minimum cross-reaction between the oligonucleotides and probes, as well as of the first ones with other sequences of nucleic acid during the amplification.

Other molecular methods that are currently used, there are some on the market to detect pathogens in food, some through DNA hybridization (Gene-Trak systems, Unipath), which is very sensitive but requires about 50 hours, and others by means of nucleic acid amplification (BAX, Dupont and FOMS Probelia, Sanofi Diagnostic Pasteur) requiring at least 24 hours. None of these methods provides results on the same day of the production of food, nor makes any quantification of the present pathogenic contamination.

Among the methods described above, in some cases it will be necessary only to increase the sensitivity of the method to detect the presence or absence of pathogens in particular reliably and rapidly, whereas in other cases it may be necessary, moreover, to further quantify pathogens that may present in order to establish the limits of concentration, starting from which the presence of the pathogen may present a problem for the consumer's health.

According to the former, it is of utmost concern to the food and health industry to have a quick method, which employs less than 5 hours, to detect and quantify simultaneously four of the most important infectious agents or pathogens, transmissible by food and/or contaminated environmental surfaces, such as *Listeria* spp, *Staphylococcus aureus, Campylobacter jejuni,* and *Escherichia coli* O157:H7. This detection and multiple, simultaneous and quick quantification of pathogens, through reaction of multiplex amplification using polymerase chain reaction in real time, will allow to save costs and time in an industry where the times on the shelf of the products are extremely important.

SUMMARY OF THE INVENTION

According to the above and in order to find solutions to the constraints encountered, it is the object of the invention to offer a method for the detection and multiple, simultaneous quantification of any combination of pathogens, selected from a group consisting of *Listeria* spp, *Staphylococcus aureus*, *Campylobacter jejuni* and *Escherichia coli* O157:H7, in one or more test samples, by multiplex amplification reaction, using real-time polymerase chain reaction (PCR), the steps of the method are: (a) extracting DNA from the test sample or samples; (b) preparing a reaction mixture specific for the pathogens to be detected and quantified, such that the reaction mixture contains the necessary reagents for enzymatic amplification of the extracted DNA and identification of the pathogens to be detected and quantified; (c) amplifying the reaction mixture by means of multiplex amplification reaction using PCR; and (d) simultaneously determining the presence or absence of and quantification of the pathogens in the test sample or samples; the method is particular in that (i) the reaction mixture for the enzymatic amplification of DNA extracted and identification of any combination of *Listeria* spp, *Staphylococcus aureus*, *Campylobacter jejuni* and/or *Escherichia coli* O157:H7 to be detected and quantified contains (a) a first pair of oligonucleotide primers identified as SEQ ID NO: 1 and SEQ ID NO: 2 and a probe identified as SEQ ID NO: 3, which react with an initial target nucleic acid sequence of *Listeria* sp; (b) a second pair of oligonucleotide primers identified as SEQ ID NO: 4 and SEQ ID NO: 5 and a probe identified as SEQ ID NO: 6, which react with a second target nucleic acid sequence of *Staphylococcus aureus*, (c) a third pair of oligonucleotide primers identified as SEQ ID NO: 7 and SEQ ID NO: 8 and a probe identified as SEQ ID NO: 9, which react with a third target nucleic acid sequence of *Campylobacter jejuni*, and/or (d) fourth pair of oligonucleotide primers identified as SEQ ID NO: 10 and SEQ ID NO: 11 and a probe identified as SEQ ID NO: 12, which react with a fourth target nucleic acid sequence of *Escherichia coli* O157:H7, (ii) the presence or absence of and quantification of said pathogens in any combination of *Listeria* spp, *Staphylococcus aureus*, *Campylobacter jejuni* and/or *Escherichia coli* O157:H7 in the test sample or samples is determined by means of a fluorescent signal or fluorescence emission specific for each pathogen.

Another object of this invention is to provide an oligonucleotide that has a nucleotide sequence selected from a group consisting of sequences identified as SEQ ID NO: 1, SEQ ID NO: 2 and SEQ ID NO: 3.

It is also the object of the invention to provide an oligonucleotide that has a nucleotide sequence selected from a group consisting of sequences identified as SEQ ID NO: 4, SEQ ID NO: 5 and SEQ ID NO: 6.

Another object of the invention is an oligonucleotide that has a nucleotide sequence selected from a group consisting of sequences identified as SEQ ID NO: 7, SEQ ID NO: 8 and SEQ ID NO: 9.

It is also the object of the invention to provide an oligonucleotide that has a nucleotide sequence selected from a group consisting of sequences identified as SEQ ID NO: 10, SEQ ID NO: 11 and SEQ ID NO: 12.

In addition to the above, it is also the object of the invention to provide a marked probe which includes an oligonucleotide identified as SEQ ID NO: 3, and at least one marker.

Another object of the invention is to provide a marked probe which includes an oligonucleotide identified as SEQ ID NO: 6, and at least one marker.

It is also the subject of a marked probe the invention which includes an oligonucleotide identified as SEQ ID NO: 9, and at least one marker.

Another object of the invention is to provide a marked probe which includes an oligonucleotide identified as SEQ ID NO: 12; and at least one marker.

Finally, it is the object of the invention to provide a diagnostic kit for the detection and multiple, simultaneous quantification of any combination of pathogens, selected from a group consisting of *Listeria* spp, *Staphylococcus aureus*, *Campylobacter jejuni* and *Escherichia coli* O157:H7, in one or more test samples, by multiplex amplification reaction, using real-time polymerase chain reaction (PCR), the diagnostic kit has (a) one or more oligonucleotides as any group of sequences identified as SEQ ID NO: 1, SEQ ID NO: 2 and SEQ ID NO: 3; SEQ ID NO: 4, SEQ ID NO: 5 and SEQ ID NO: 6; SEQ ID NO: 7, SEQ ID NO: 8 and SEQ ID NO: 9; and/or SEQ ID NO: 10, SEQ ID NO: 11 and SEQ ID NO: 12; (b) one or more marked probes that contain any of the oligonucleotides with its sequences identified as SEQ ID NO: 3, SEQ ID NO: 6, SEQ ID NO: 9 and SEQ ID NO: 12; and a different marker for each sequence, and (c) other reagents or compositions needed to perform the test.

BRIEF DESCRIPTION OF THE FIGURES

The characteristic details of the invention are described in the following paragraphs together with the figures that accompany it, which are for the purpose of defining the invention but not limiting its scope.

DETAILED DESCRIPTION OF THE INVENTION

The term "enzymatic amplification of DNA," as used in the context of this description, means the use of polymerase chain reaction (PCR) to increase the concentration of a particular DNA sequence within a combination of DNA sequences. The particular sequence of DNA that is amplified is referred to as a "target sequence."

The term "pair of primers" is employed under the meaning of a pair of oligonucleotide that are complementary to the sequences bordering the target sequence. The pair of primers is an "upstream" primer which has a nucleic acid sequence that is complementary to a sequence "upstream" of the target sequence, and a "downstream" primer which has a nucleic acid sequence that is a sequence complementary to "downstream" of the target sequence.

The term "multiplex amplification reaction" means, in the context of this description, amplified by PCR procedure, multiple target sequences of DNA in a test sample in particular.

In the present invention four bacteria were detected and quantified simultaneously using the technique of real-time PCR, which compared with other techniques, does not require a pre-enrichment, nor preparing a series of tubes with a mixture of a specific reaction for each bacteria to be detected; it is necessary to stress that it is a breakthrough that four bacteria are detected simultaneously the total time of analysis is reduced to 2.5 hrs minimum, representing a competitive advantage in decreasing the cost of analysis, using the same mixture for the detection test. Additionally, better sensitivity was achieved, as the sample preparation (which is already included in the 2.5 hrs time) has given better results because it has been adapted so that there are no factors that could adversely affect the amplification.

The method provided by this invention allows detecting, identifying and quantifying multiple pathogens simultaneously transmissible via food, contaminated surfaces or environments, such as *Listeria* spp, *Staphylococcus aureus*, *Campylobacter jejuni* and/or *Escherichia coli* O157:H7, in one or more test samples, through multiplex amplification reaction using polymerase chain reaction in real time. The test sample can be any sample that contains DNA and you want to know the possible contamination of by said pathogens. In a particular realization, said test sample is a sample of a food product, for example, meat and milk products, or a sample of contaminated surfaces or environments.

Oligonucleotides: Design and Information of Sequence

The oligonucleotides of the invention have been designed in order to identify specifically, *Listeria* spp, *Staphylococcus aureus*, *Campylobacter jejuni* and *Escherichia coli* O157:H7 that may be present in a sample test without giving false positives because of the presence of other pathogens it may contain.

There is a couple of oligonucleotide primers for each of the pathogens to be identified (*Listeria* spp, *Staphylococcus aureus*, *Campylobacter jejuni* and *Escherichia coli* O157:H7), so that each pair of primers comprises a first synthetic nucleotide "upstream" sequence complementary to a nucleotide "upstream" sequence which borders the extreme 5' of a nucleic acid sequence target, and a second synthetic nucleotide "downstream" sequence, complementary to a "downstream" sequence which borders the extreme 3' of the nucleic acid sequence target. Nucleotide sequences should have every pair of oligonucleotide primers which are specific to the pathogen to be detected, so that they do not react or are crossed with other pathogens. Also, for each of the pathogens to be identified, a synthetic sequence of a probe test is developed. Oligonucleotides developed are shown in Table 1.

TABLE 1

| Identifier | Type | Pathogen | Nucleotide Sequence |
|---|---|---|---|
| SEQ ID NO: 1 | "upstream" primer F | *Listeria* spp | CTTGACATCCTTTGACCACTCTG |
| SEQ ID NO: 2 | "downstream" primer F | *Listeria* spp | GACTTAACCCAACATCTCACGAC |
| SEQ ID NO: 3 | P test | *Listeria* spp | AGCTGACGACAACCATGCACCACC |
| SEQ ID NO: 4 | "upstream" primer F | *Staphylococcus aureus* | AACAAAACAGACCATCTTTAAGCG |
| SEQ ID NO: 5 | "downstream" primer R | *Staphylococcus aureus* | AGATGAGCTACCTTCAAGACCTTC |
| SEQ ID NO: 6 | P test | *Staphylococcus aureus* | ACTCAACCGACGACACCGAACCCT |
| SEQ ID NO: 7 | "upstream" primer F | *Campylobacter jejuni* | GCAGCAGTAGGGAATATTGCG |
| SEQ ID NO: 8 | "downstream" primer R | *Campylobacter jejuni* | TACGCTCCGAAAAGTGTCATCC |
| SEQ ID NO: 9 | P test | *Campylobacter jejuni* | AACCCTGACGCAGCAACGCCGC |
| SEQ ID NO: 10 | "upstream" primer F | *Escherichia coli* O157:H7 | GCAGATAAACTCATCGAAACAAGG |
| SEQ ID NO: 11 | "downstream" primer R | *Escherichia coli* O157:H7 | TAAATTAATTCCACGCCAACCAAG |
| SEQ ID NO: 12 | P test | *Escherichia coli* O157:H7 | ACCCTGTCCACACGATGCCAATGT |

In a preferential embodiment of the invention sequences SEQ ID NO: 3, SEQ ID NO: 6, SEQ ID NO: 9 and SEQ ID NO: 12, used as test probes are marked in their 5' extreme with a fluorophore or a dye capable of emitting energy, and at its 3' end with an extinguisher or a dye capable of capturing the energy emitted by the fluorophore excitation. The fluorophores and dyes, used as markers to detect and identify *Listeria* spp, *Staphylococcus aureus*, *Campylobacter jejuni* and *Escherichia coli* O157:H7 without producing cross-reactions between them and other components are shown in Table 2.

TABLE 2

| Identifier | Pathogen | Nucleotide Sequence | Fluorophore for marking at 5' end | Dye for marking at 3' end |
|---|---|---|---|---|
| SEQ ID NO: 3 | Listeria spp | AGCTGACGACAACCATGCACCACC | TET | BHQ-1 |
| SEQ ID NO: 6 | Staphylococcus aureus | ACTCAACCGACGACACCGAACCCT | TxR | BHQ-2 |
| SEQ ID NO: 9 | Campylobacter jejuni | AACCCTGACGCAGCAACGCCGC | Cy5 | BHQ-3 |
| SEQ ID NO: 12 | Escherichia coli O157:H7 | ACCCTGTCCACACGATGCCAATGT | FAM | BHQ-1 |

Sample Preparation or DNA Test Samples

To develop the methodology of the invention the following steps are considered for the preparation of a test sample:

First, there is a stage of washing, where a food sample, environmental or surface area is subject to a saline solution forming a suspension which was subsequently centrifuged to obtain a first sediment obtained by the elimination of water-soluble substances present in the suspension.

Once the sediment of the sample is obtained, it is incubated with lysozyme to break down the cell wall of the bacteria present in the sample, then proceed with an incubation with proteinase K to cause the hydrolysis of proteins and the lysozyme previously added.

The extraction of proteins and other fat-soluble compounds present is performed through the application of phenol-chloroform-alcohol, so that once extracted, through a precipitation with ethanol, a selective precipitation of the DNA present is performed, forming a concentration of DNA that is dried.

Finally, with the concentration of DNA obtained, a suspension is formed that is heated to approximately 65° C., which causes a quick dissolution of the DNA sample.

In each of the elements tested, quantity tests of added reagent were performed, times of centrifuge-incubation, repetition of the washings, until finding the optimal conditions. The sample preparation was done taking into account that all the reagents and samples should be kept at a cooling temperature during its process.

Examples of the preparation process of the sample or test samples for DNA are described below:

EXAMPLE 1

Preparation of a DNA Sample Starting from a Sample of Food of Cheese or Meat Products 1. Place 25 grams of sampled food in a conical sterile tube of 50 ml, and emerging to 40 ml with a sterile saline solution at room temperature.
2. Allow the tube to rest with the food sample for 10 minutes in an upright position.
3. Remove the food, centrifuge at 3,500 min$^{-1}$ (rpm) for 15 minutes and extract the supernatant carefully so as not to lose the sediment.
4. Stir the sediment in the vortex for 10 seconds.
5. Transfer all of the sediment to a 2 ml Eppendorf tube, rinse the conical tube with 1 ml of sterile saline and collect the washing with what was previously obtained.
6. Centrifuge at 14,000 min$^{-1}$ (rpm) for 8 minutes.
7. Remove all the supernatant with an automatic pipette.
8. Add 100 µl of Tris-HCl 100 mmol and pH=8, and 30 µl of lysozyme, and mix in the vortex for 10 seconds.
9. Incubate at 37° C. for 30 minutes in a water bath.
10. Add 100 µl of TE 1× with SDS at 1% and 3 µl of Proteinase K (20 mg/ml).
11. Mix and incubate at 55° C. for 30 minutes.
12. Add 500 µl of phenol-chloroform-isoamyl alcohol (24:24:1) and 100 µl of TE 1× and stir 5 minutes for inversion.
13. Centrifuge for 8 minutes at 13,500 min$^{-1}$ (rpm) and transfer 250 µl of the upper phase to another tube.
14. Add 582.5 µl of absolute ethanol and keep it in the freezer for 10 minutes.
15. Centrifuge for 8 minutes at 13,500 min$^{-1}$ (rpm).
16. Decant and dry.
17. Dissolve again in 25 µl of TE 1× and ensure that the button DNA is dissolved.
18. Heat to 65° C. for 15 minutes.
19. Leave at room temperature for 30 minutes and process.

EXAMPLE 2

Preparation of a DNA Sample Starting from an Environmental or a Surface Sample

1. Wiping a sterile sponge over an area of 20 cm×20 cm that is to be analyzed to obtain a sample.
2. Squeeze the sponge in a bag in order to decant the liquid into a conical tube of 50 ml, and emerge a sterile saline solution of 40 ml.
3. Centrifuge at 3,500 min$^{-1}$ (rpm) for 15 minutes and extract the supernatant carefully so as not to lose the sediment.
4. Stir the sediment in the vortex for 10 seconds.
5. Transfer all of the sediment to a 2 ml Eppendorf tube. Rinse the conical tube with 1 ml of sterile saline and mix the washing with the one previously obtained.
6. Centrifuge at 14,000 min$^{-1}$ (rpm) for 8 minutes.
7. Wash 2 more times with 1.5 ml of sterile saline solution.
8. Remove all the supernatant with an automatic pipette.
9. Add 100 µl of Tris-HCl 100 mmol and pH=8, and 30 µl of lysozyme, and mix in the vortex for 10 seconds.
10. Incubate at 37° C. for 30 minutes in a water bath.
11. Add 100 µl of TE 1× with SDS at 1% and 3 µl of Proteinase K (20 mg/ml).
12. Mix and incubate at 55° C. for 30 minutes.
13. Add 500 µl of phenol-chloroform-isoamyl alcohol (24:24:1) and 100 µl of TE 1× and stir 5 minutes for inversion.
14. Centrifuge for 8 minutes at 13,500 min$^{-1}$ (rpm) and transfer 250 µl of the upper phase to another tube.
15. Add 582.5 µl of absolute ethanol and keep it in the freezer for 10 minutes.

16. Centrifuge for 8 minutes at 13,500 min$^{-1}$ (rpm).
17. Decant and dry.
18. Dissolve again in 25 µl of TE 1×. Make sure the DNA button is dissolved.
19. Heat to 65° C. for 15 minutes.
20. Leave at room temperature for 30 minutes and process.

Preparation of the Reaction Mix

Once the sample or test samples of DNA are obtained, a reaction mix is prepared using components described in Table 3.

TABLE 3

| Component of the Reaction Mix | | Initial Concentration | Amount to add (µl) | Final Concentration |
|---|---|---|---|---|
| | MgCl$_2$ | 50 mmol | 1.75 | 3.5 |
| | DNTPs | 10 mmol | 0.5 | 200 µmol |
| | Buffer | 10X | 3.75 | 1.5X |
| Listeria spp | SEQ ID NO: 1 | 5 nmol | 1 | 200 pmol |
| | SEQ ID NO: 2 | 5 nmol | 1 | 200 pmol |
| | SEQ ID NO: 3 | 5 nmol | 0.25 | 50 pmol |
| Staphylococcus aureus | SEQ ID NO: 4 | 5 nmol | 1 | 200 pmol |
| | SEQ ID NO: 5 | 5 nmol | 1 | 200 pmol |
| | SEQ ID NO: 6 | 5 nmol | 0.25 | 50 pmol |
| Campylobacter jejuni | SEQ ID NO: 7 | 5 nmol | 1.5 | 300 pmol |
| | SEQ ID NO: 8 | 5 nmol | 1.5 | 200 pmol |
| | SEQ ID NO: 9 | 5 nmol | 1.75 | 350 pmol |
| Escherichia coli O157: H7 | SEQ ID NO: 10 | 5 nmol | 1 | 200 pmol |
| | SEQ ID NO: 11 | 5 nmol | 1 | 200 pmol |
| | SEQ ID NO: 12 | 5 nmol | 0.25 | 50 pmol |
| | Taq DNA polymerase | 5 U/µl | 0.25 | |
| | Water | | 2.25 | |
| | DNA Test Sample | | 5 | |
| | Total Volume | | 25 | |

Subsequently, a cocktail of reaction was prepared for 100 reactions by mixing the ingredients described in Table 4.

TABLE 4

| Component of the Reaction Mix | | Amount to add (µl) for one Reaction | Amount to add (µl) for 100 Reactions |
|---|---|---|---|
| | MgCl$_2$ | 1.75 | 175 |
| | DNTPs | 0.5 | 50 |
| | Buffer | 3.75 | 375 |
| Listeria spp | SEQ ID NO: 1 | 1 | 100 |
| | SEQ ID NO: 2 | 1 | 100 |
| | SEQ ID NO: 3 | 0.25 | 25 |
| Staphylococcus aureus | SEQ ID NO: 4 | 1 | 100 |
| | SEQ ID NO: 5 | 1 | 100 |
| | SEQ ID NO: 6 | 0.25 | 25 |
| Campylobacter jejuni | SEQ ID NO: 7 | 1.5 | 150 |
| | SEQ ID NO: 8 | 1.5 | 150 |
| | SEQ ID NO: 9 | 1.75 | 175 |
| Escherichia coli O157: H7 | SEQ ID NO: 10 | 1 | 100 |
| | SEQ ID NO: 11 | 1 | 100 |
| | SEQ ID NO: 12 | 0.25 | 25 |
| | Water | 2.25 | 225 |
| | DNA Test Sample | 5 | |

The cocktail prepared mixes perfectly by inversion and 19.75 µl are dispensed Eppendorf flasks of 0.5 ml to be stored, frozen, and protected from light.

Reaction of Multiplex Amplification Using PCR in Real-Time and Detection and Quantification of Pathogens In a preferential embodiment of the invention, the multiplex amplification reaction using PCR in real-time provides many advantages over the conventional PCR method to detect a single target. The multiplex amplification reaction using multiplex PCR requires the development of oligonucleotide primers and probes, specific for the target sequence of the pathogen to be detected, so that said oligonucleotide primers and probes be compatible with one another within the same optimum temperature of 40° C. to 65° C. and submitted to the same conditions of chemical reaction in order to allow the annealing by hybridization of two segments of complementary nucleic acid. In addition to this, the sets of oligonucleotide primers and probes should not cross-react or anneal during the amplification to other nucleic acid sequences for which they were not designed.

Given the above, the following pairs of oligonucleotide primers are used to amplify each of the target nucleic acid sequences of each pathogen to be detected. A pair of oligonucleotide primers of Listeria spp identified as SEQ ID NO: 1 and SEQ ID NO: 2, which anneals to a target sequence of the genome of Listeria spp. A pair of oligonucleotide primers of Staphylococcus aureus identified as SEQ ID NO: 4 and SEQ ID NO: 5 which anneals to a target sequence of the genome of Staphylococcus aureus. A pair of oligonucleotide primers of Campylobacter jejuni identified as SEQ ID NO: 7 and SEQ ID NO: 8 which anneals to a target sequence of the genome of Campylobacter jejuni. And a pair of oligonucleotide primers of Escherichia coli O157:H7 identified as SEQ ID NO: 10 and SEQ ID NO: 11, which anneals to a target sequence of the genome of Escherichia coli O157:H7.

Each probe identified as SEQ ID NO: 3, SEQ ID NO: 6, SEQ ID NO: 9 and SEQ ID NO: 12, which is used in the multiplex amplification reaction using PCR in real-time, is a double-marked oligonucleotide sequence that is complementary to each of the intermediate sequences in the amplified products that were obtained. Each of the probes is marked on its 5' end with a fluorophore or a dye capable of emitting energy, and on its 3' end with an extinguisher or a dye, capable of capturing the energy emitted by the excitation of said fluorophore, as described by Nazarenko et al. in the U.S. Pat. No. 5,866,336 which mentions fluorophores that transfer energy and how these are applied in the oligonucleotide primers in the methods of nucleic amplification.

In a preferential embodiment of the invention, the fluorophores used are TET, TxR, Cy5, FAM, while the dyes are BHQ-1, BHQ-2 and BHQ-3. So that the oligonucleotide sequences used as probes (SEQ ID NO: 3, SEQ ID NO: 6, SEQ ID NO: 9 and SEQ ID NO: 12) are marked on their 5' and 3' ends according to the combination shown in Table 2 above.

In one particular example of embodiment, the DNA sample is prepared for its amplification under the following conditions:

Sample of milk or of environment: A flask was defrosted with 19.75 µl of a cocktail prepared and added 0.25 µl of Taq DNA polymerase, 4 µl of water and 1 µl of the sample of DNA to be analyzed.

Sample of meat or cheese: A flask was defrosted with 19.75 µl of a cocktail prepared and added 0.25 µl of Taq DNA polymerase, 5 µl of the sample of DNA to be analyzed.

The multiplex amplification reaction using PCR is performed on an apparatus for the simultaneous control of multiple nucleic acid amplifications, as the device described by Russell G. Higuchi and Robert M. Watson in the publication of the European Patent EP-640,828, which usually consists of a thermal cycler with a plurality of holes where tubes are introduced containing the reaction mixture for the enzymatic amplification of DNA from pathogens to be detected and identified; a light source coupled to the thermal cycler and adapted to distribute the light on the plurality of holes, and a sensor or fluorescence detector adapted to simultaneously detect the emitted light.

Figure 1:
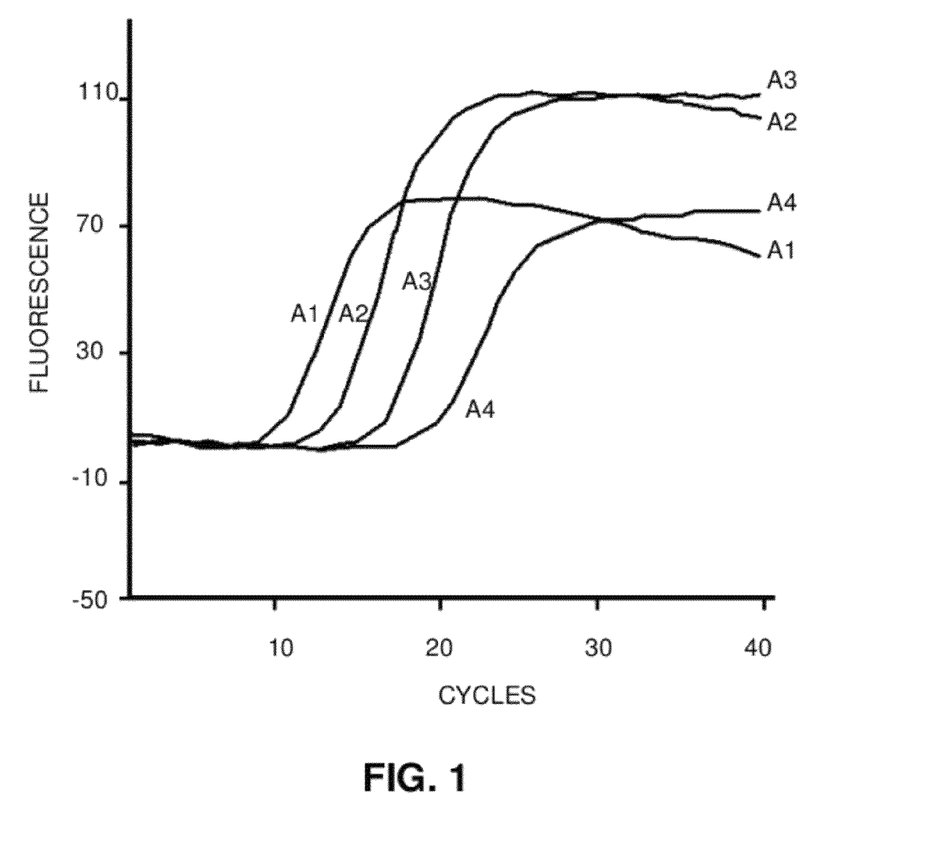
FIG. 1 illustrates a calibration curve for *Listeria* spp according to the invention, where A1: is a reference to increased concentration; A4: is a reference of a lesser concentration. The reading of a sample is interpolated in the readings of the references to know the CFU/ml.
Figure 2:
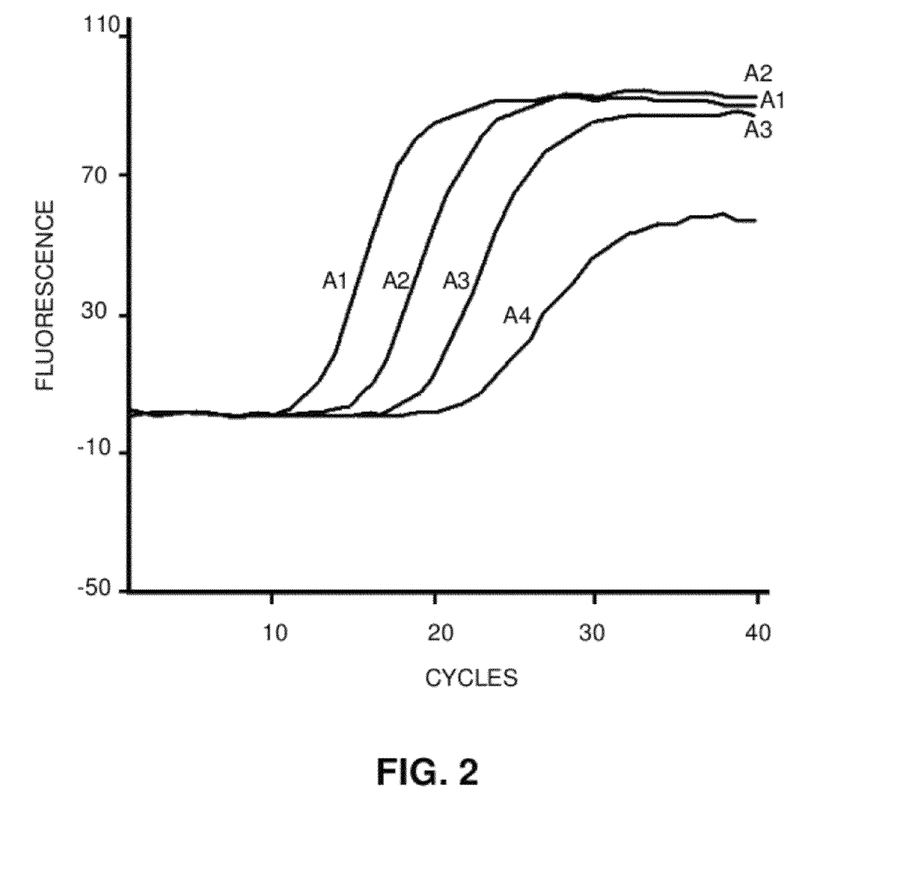
FIG. 2 illustrates a calibration curve for *Staphylococcus aureus* according to the invention, where A1: is a reference to increased concentration; A4: is a reference of a lesser concentration. The reading of a sample is interpolated in the readings of the references to know the CFU/ml.
Figure 3:
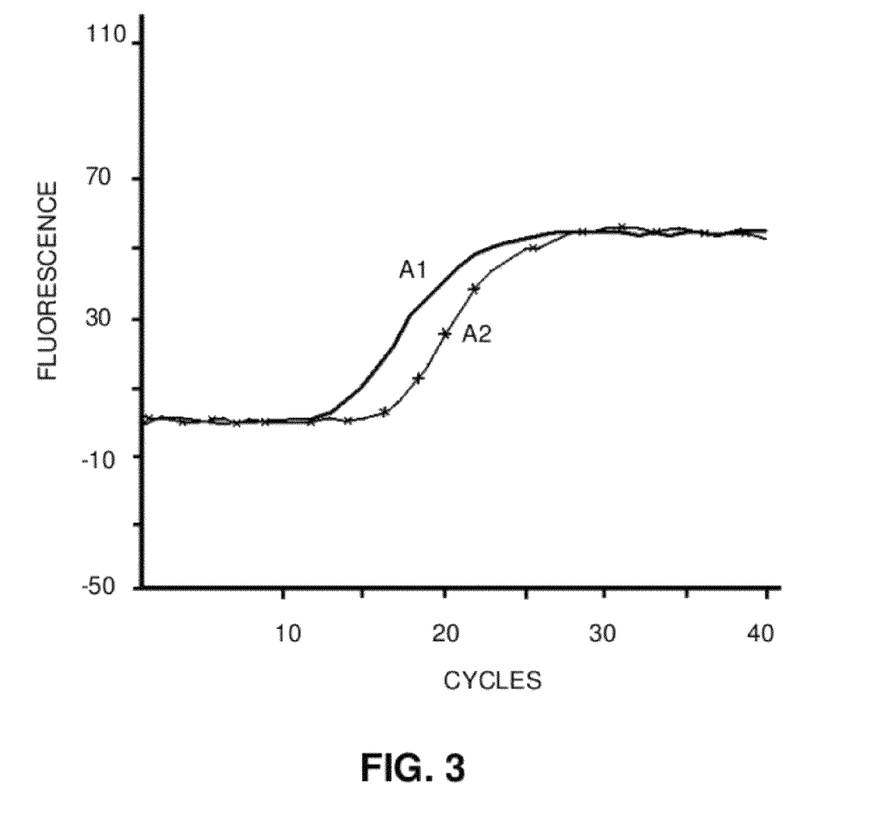
FIG. 3 illustrates a calibration curve for *Campylobacter jejuni* according to the invention, where A1: is a reference to increased concentration; A2: is a reference of a lesser concentration. The reading of a sample is interpolated in the readings of the references to know the CFU/ml.
Figure 4:
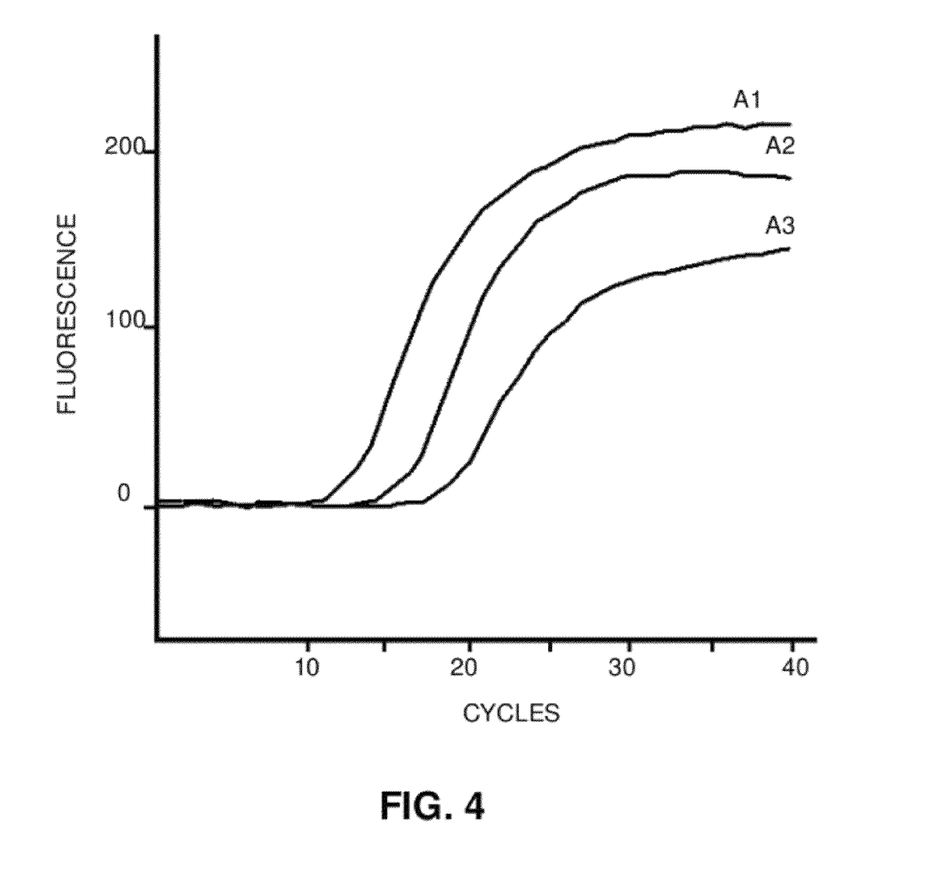
FIG. 4 illustrates a calibration curve for *Escherichia coli* O157:H7 according to the invention, where A1: is a reference to increased concentration; A3: is a reference of a lesser concentration. The reading of a sample is interpolated in the readings of the references to know the CFU/ml.

In order to quantify the micro-organism present in the sample, calibration curves are produced, preparing suspensions of each of the pathogens to be detected (Listeria spp, Staphylococcus aureus, Campylobacter jejuni and Escherichia coli O157:H7), adjusting the turbidity in the McFarland tube of 0.5 to prepare dilutions to $10^{-1}$, $10^{-2}$, $10^{-3}$, $10^{-4}$, $10^{-5}$, $10^{-6}$, $10^{-7}$ and $10^{-8}$ and then contaminate 25 grams of food with each of these suspensions (one food for each dilution). Then, proceed to the extraction of DNA as if it were a sample and an account is prepared on a plate of each of the dilutions prepared to be submitted to the thermal cycler, assigning the corresponding concentration of pathogens. Finally, the curve of cT against log ug/g is built, thereby obtaining a calibration curve for *Listeria* spp (see FIG. 1), *Staphylococcus aureus* (see FIG. 2), *Campylobacter jejuni* (see FIG. 3) and *Escherichia coli* O157:H7 (see FIG. 4).

In one particular embodiment, the apparatus used comprises a fast thermal cycler in real-time coupled to a fluorescence detection system, allowing real-time monitoring of the process of amplification after each cycle. An example of the thermal cycler used in the method of the invention is the cycler SMART CYCLER® II of CEPHEID®.

Detection and Quantification of Pathogens Present in the DNA Sample

The presence or absence and quantification of pathogens in any combination of *Listeria* spp, *Staphylococcus aureus*, *Campylobacter jejuni* and/or *Escherichia coli* O157:H7 in a sample or test samples is determined by a fluorescent signal or emission of specific fluorescence of each product or amplified DNA sample. Therefore, a specific wave length is pointed out for the excitation of each fluorescence and its emission at specific wavelengths is detected.

Results

In an example of embodiment, Table 5 presents the conditions in which the multiplex amplification reaction was carried out, Table 6 presents the detection limits, and Table 7

TABLE 6

| Sample type | *Listeria* spp | *Staphylococcus aureus* | *Campylobacter jejuni* | *Escherichia coli* O157: H7 |
|---|---|---|---|---|
| FOOD | | | | |
| Meat and Cheese (genomic units/grams). | 1 | 3 | 160 | 16 |
| ENVIRONMENT | | | | |
| Drainage (genomic units/sample) | 1 | 3 | 160 | 16 |
| Floors (genomic units/sample) | 1 | 3 | 160 | 16 |
| Surface contact (genomic units/sample) | 1 | 3 | 160 | 16 |
| Walls (genomic units/sample) | 1 | 3 | 160 | 16 |
| Operators (genomic units/sample) | 1 | 3 | 160 | 16 |

TABLE 7

| | *Listeria* spp | | *Staphylococcus aureus* | | *Campylobacter jejuni* | | *Escherichia coli* O157:H7 | |
|---|---|---|---|---|---|---|---|---|
| Benchmark | (CFU/ml) | Reading | (CFU/ml) | Reading | (CFU/ml) | Reading | (CFU/ml) | Reading |
| A1 | 10000000 | 12.72 | 10000000 | 14.98 | 1000000 | 15.50 | 1000000 | 13.8 |
| A2 | 1000000 | 15.5 | 1000000 | 18.48 | 100000 | 17.50 | 100000 | 17.2 |
| A3 | 100000 | 18.86 | 100000 | 22.34 | 0 | 0 | 10000 | 20.4 |
| A4 | 10000 | 22.69 | 10000 | 28.51 | 0 | 0 | 0 | 0 | shows the readings of concentrations that were obtained as a result of detection and quantification of the four pathogens (*Listeria* spp, *Staphylococcus aureus*, *Campylobacter jejuni* and/or *Escherichia coli* O157:H7) simultaneously in samples of cold meats, dairy and atmosphere, using only one device with a single mixture of reagents and four specific oligonucleotides for different pathogens to a single condition of temperatures and mixing for their amplification. Also, the FIGS. 1, 2, 3, and 4 graphically show their identification and quantification.

TABLE 5

| | Temperature (° C.) | Time (seconds) | Cycles |
|---|---|---|---|
| Initial Process | 94 | 120 | 1 |
| Amplification | 94 | 15 | 40 |
| | 63 | 25 | |

The method of the present invention does not require a pre-enrichment, therefore, the process time is much shorter, approximately 2.5 hours, and has the capacity to detect and quantify possible pathogens cultivable, apart from possible pathogens non-cultivable in a simultaneous manner.

Diagnostics Set

In general, the diagnostics sets of the invention contain each of the pairs of oligonucleotide primers corresponding to each of the pathogens to be detected (*Listeria* spp, *Staphylococcus aureus*, *Campylobacter jejuni* and/or *Escherichia coli* O157:H7), just as each of the probes marked for each of said pathogens, in order to be able to make a choice between performing the detection of a single pathogen (using only the pair of oligonucleotide primers and its probe marked), or for the simultaneous or combined detection of the four pathogens mentioned, depending on the necessities.

The diagnostics kits provided by this invention may be presented in the form of a box containing, in addition to some containers with the pairs of oligonucleotide primers and/or marked probes mentioned previously, some containers with the totality or part of the rest of the reagents needed to perform said method, for example, ultrapure water, dNTPs (dATP, dCTP, dGTP, and dTTP), an appropriate buffer for the enzymatic amplification reaction, a thermostable DNA polymerase (e.g., Taq DNA polymerase), a magnesium salts (for example, MgCl$_2$), among others. Additionally and optionally, the diagnostics sets provided by this invention may include some containers with DNA from *Listeria* sp, *Staphylococcus aureus*, *Campylobacter jejuni* and/or *Escherichia coli* O157: H7 for their use as positive controls.

Based on the embodiments described above, it is considered that the modifications to the environments of the described embodiment, as well as to the environments of alternate embodiments will be considered evident for an expert in the state of the art under the present description. Therefore, it is considered that the claims cover those modifications and alternatives that are within the scope of the present invention or its equivalents.

The invention claimed is:

1. A method for detecting *Listeria* spp, *Staphylococcus aureus*, *Campylobacter jejuni*, and *Escherichia coli* O157:H7 in a food or environment sample, the method comprising the steps of:
 a) extracting DNA present in said food or environment sample;
 b) preparing a reaction mixture including said extracted DNA of said food or environment sample, a first pair of oligonucleotide primers consisting of an upstream primer of SEQ ID NO: 1 and a downstream primer of SEQ ID NO: 2, which anneals to a first target nucleic acid sequence of *Listeria* spp, a second pair of oligonucleotide primers consisting of an upstream primer of SEQ ID NO: 4 and a downstream primer of SEQ ID NO: 5, which anneals to a second target nucleic acid sequence of *Staphylococcus aureus*, a third pair of oligonucleotide primers consisting of an upstream primer of SEQ ID NO: 7 and a downstream primer of SEQ ID NO: 8, which anneals to a third target nucleic acid sequence of *Campylobacter jejuni*, a fourth pair of oligonucleotide primers consisting of an upstream primer of SEQ ID NO: 10 and a downstream primer of SEQ ID NO: 11, which anneals to a fourth target nucleic acid sequence of *Escherichia coli* O157:H7, a probe consisting of SEQ ID NO: 3 which is complementary to a sequence within the first target nucleic acid sequence of *Listeria* sp and is marked at its 5' end with TET and at its 3' end with BHQ-1, a probe consisting of SEQ ID NO: 6 which is complementary to a sequence within the second target nucleic acid sequence of *Staphylococcus aureus* and is marked at its 5' end with T×R and at its 3' end with BHQ-2, a probe consisting of SEQ ID NO: 9 which is complementary to a sequence within the third target nucleic acid sequence of *Campylobacter jejuni* and is marked at its 5' end with Cy5 and at its 3' end with BHQ-3, a probe consisting of SEQ ID NO: 12 which is complementary to a sequence within the fourth target nucleic acid sequence of *Escherichia coli* O157:H7 and is marked at its 5' end with FAM and at its 3' end with BHQ-1, and four deoxynucleotide triphosphates (dNTPs) selected from the group consisting of adenosine deoxynucleotide triphosphate (dATP), guanosine deoxynucleotide triphosphate (dGTP), thymidine deoxynucleotide triphosphate (dTTP), cytosine deoxynucleotide triphosphate (dCTP), and nucleotide analogs thereof;
 c) providing a thermostable DNA polymerase and a magnesium salt;
 d) amplifying by multiplex amplification reaction using real-time polymerase chain reaction (PCR), the first target nucleic acid sequence of *Listeria* spp, the second target nucleic acid sequence of *Staphylococcus aureus*, the third target nucleic acid sequence of *Campylobacter jejuni*, and the fourth target nucleic acid sequence of *Escherichia coli* O157:H7 from the extracted DNA of pathogens of said food or environment sample in the reaction mixture under suitable PCR reaction mixture temperature conditions by a repetitive series of PCR cycling steps by annealing the oligonucleotide primers of the step (b) to the extracted DNA and extending the annealed the oligonucleotide primers with the four deoxynucleotide triphosphates (dNTPs), the DNA polymerase and the magnesium salt, to provide amplified PCR products; and
 e) following amplification, determining the presence or absence of the first, second, third and fourth target nucleic acids in the amplified PCR products by means of a fluorescent signal or fluorescence emission specific for each target nucleic acid; and
wherein the *Listeria* spp, *Staphylococcus aureus*, *Campylobacter jejuni* and *Escherichia coli* O157:H7 are simultaneously detected and quantified in said food or environment sample.

2. The method of claim 1, wherein said reaction mixture comprises:
 at least 200 pmol of the upstream primer of SEQ ID NO: 1;
 at least 200 pmol of the downstream primer of SEQ ID NO: 2;
 at least 50 pmol of the probe of SEQ ID NO: 3;
 at least 200 pmol of the upstream primer of SEQ ID NO: 4;
 at least 200 pmol of the downstream primer of SEQ ID NO: 5;
 at least 50 pmol of the probe of SEQ ID NO: 6;
 at least 300 pmol of the upstream primer of SEQ ID NO: 7;
 at least 200 pmol of the downstream primer of SEQ ID NO: 8;
 at least 350 pmol of the probe of SEQ ID NO: 9;
 at least 200 pmol of the upstream primer of SEQ ID NO: 10;
 at least 200 pmol of the downstream primer of SEQ ID NO: 11;
 at least 50 pmol of the probe of SEQ ID NO: 12;
 at least 200 µmol of deoxynucleotide triphosphates (dNTPs);
 at least 3.5 µl of magnesium salt; and
 at least 5 µl of extracted DNA from said food or environment sample.

3. The method of claim 1, wherein the thermostable DNA polymerase is Taq.

4. The method of claim 1, wherein the magnesium salt is magnesium chloride.

5. A diagnostics kit for multiple and simultaneously detecting and quantifying of *Listeria* spp, *Staphylococcus aureus*, *Campylobacter jejuni* and *Escherichia coli* O157:H7 in a food or environment sample, by multiplex amplification reaction, using real-time polymerase chain reaction (PCR), the diagnostics kit comprising:
 a first pair of oligonucleotide primers consisting of an upstream primer of SEQ ID NO: 1 and a downstream primer of SEQ ID NO: 2, which anneals to a first target nucleic acid sequence of *Listeria* spp;
 a second pair of oligonucleotide primers consisting of an upstream primer of SEQ ID NO: 4 and a downstream primer of SEQ ID NO: 5, which anneals to a second target nucleic acid sequence of *Staphylococcus aureus*;

a third pair of oligonucleotide primers consisting of an upstream primer of SEQ ID NO: 7 and a downstream primer of SEQ ID NO: 8, which anneals to a third target nucleic acid sequence of *Campylobacter jejuni;* a fourth pair of oligonucleotide primers consisting of an upstream primer of SEQ ID NO: 10 and a downstream primer of SEQ ID NO: 11, which anneals to a fourth target nucleic acid sequence of *Escherichia coli* O157: H7;

a probe consisting of SEQ ID NO: 3 which is complementary to a sequence within the first target nucleic acid sequence of *Listeria* spp, which is marked at its 5' end with TET and at its 3' end with BHQ-1;

a probe consisting of SEQ ID NO: 6 which is complementary to a sequence within the second target nucleic acid sequence of *Staphylococcus aureus*, which is marked at its 5' end with TxR and at its 3' end with BHQ-2;

a probe consisting of SEQ ID NO: 9 which is complementary to a sequence within the third target nucleic acid sequence of *Campylobacter jejuni*, which is marked at its 5' end with Cy5 and at its 3' end with BHQ-3;

a probe consisting of SEQ ID NO: 12 which is complementary to a sequence within the fourth target nucleic acid sequence of *Escherichia coli* O157:H7, which is marked at its 5' end with FAM and at its 3' end with BHQ-1;

four deoxynucleotide triphosphates (dNTPs) selected from the group consisting of adenosine deoxynucleotide triphosphate (dATP), guanosine deoxynucleotide triphosphate (dGTP), thymidine deoxynucleotide triphosphate (dTTP), cytosine deoxynucleotide triphosphate (dCTP), and nucleotide analogs thereof;

thermostable DNA polymerase; and magnesium chloride.

* * * * *